United States Patent
Ito et al.

(10) Patent No.: US 9,550,724 B2
(45) Date of Patent: Jan. 24, 2017

(54) DIPHENYLAMINE COMPOUNDS AND PRODUCTION METHOD THEREOF

(71) Applicants: IHARA CHEMICAL INDUSTRY CO., LTD., Tokyo (JP); KUMIAI CHEMICAL INDUSTRY CO., LTD., Tokyo (JP)

(72) Inventors: Minoru Ito, Iwata (JP); Akiko Ikumi, Fuji (JP)

(73) Assignees: IHARA CHEMICAL INDUSTRY CO., LTD., Tokyo (JP); KUMIAI CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/361,313

(22) PCT Filed: Dec. 5, 2012

(86) PCT No.: PCT/JP2012/081492
§ 371 (c)(1),
(2) Date: May 29, 2014

(87) PCT Pub. No.: WO2013/089002
PCT Pub. Date: Jun. 20, 2013

(65) Prior Publication Data
US 2014/0336415 A1    Nov. 13, 2014

(30) Foreign Application Priority Data
Dec. 14, 2011    (JP) .................................. 2011-273666

(51) Int. Cl.
C07C 209/10    (2006.01)
C07C 213/02    (2006.01)
C07C 211/56    (2006.01)
C07C 217/92    (2006.01)

(52) U.S. Cl.
CPC ........... C07C 209/10 (2013.01); C07C 211/56 (2013.01); C07C 213/02 (2013.01); C07C 217/92 (2013.01)

(58) Field of Classification Search
None
See application file for complete search history.

(56) References Cited

U.S. PATENT DOCUMENTS 9,061,967 B2 * 6/2015 Liu ....................... A01N 33/18
2003/0236260 A1 12/2003 Shimojo et al.

FOREIGN PATENT DOCUMENTS

| JP | S52114000 A | 9/1977 |
| JP | S58113151 A | 7/1983 |
| JP | H01186849 A | 7/1989 |
| JP | WO2011116671 | * 9/2011 ........... C07C 211/56 |
| WO | 2009016841 | 2/2009 |

OTHER PUBLICATIONS

Borodkin, V.F., "Chloro Derivatives of 2-Nitrodiphenylamine" Zhurnal Prikladnoi Khimii, vol. 21, No. 10, 1948, p. 987-994.
(Continued)

*Primary Examiner* — Clinton Brooks
(74) *Attorney, Agent, or Firm* — Nath, Goldberg & Meyer; Tanya E. Harkins

(57) ABSTRACT

An inexpensive and convenient production method of diphenylamine compounds is provided, that can solve problems in the conventional technology such as decrease in reactivity, restriction of substituents, high temperature, high pressure, by-products or the like. Further, diphenylamine compounds useful as intermediates of medicine and agricultural chemicals are provided. Diphenylamine compounds are produced, represented by general formula (3):

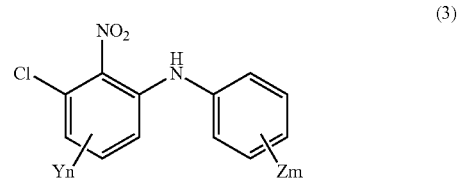

which is characterized by reacting aniline compounds represented by general formula (2):

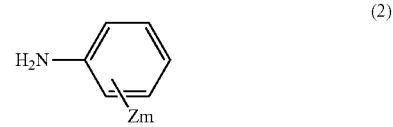

under the presence of base and ethers solvent, with 2,6-dichloronitrobenzene compound represented by general formula (1):

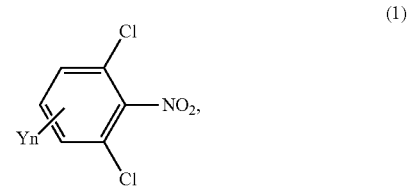

and a diphenylamine compound represented by general formula (3).

5 Claims, No Drawings

(56) References Cited

OTHER PUBLICATIONS

Irie, Y., et al., "O-Amine-Assisted Cannizzaro Reaction of Glyoxal with New 2, 6-Diaminoanilanes", European Journal of Organic Chemistry, No. 14, 2009, pp. 2243-2250.
Wrobel, Z., et al., "Simple Synthesis of N-Aryl-2-nitrosoanilines in the Reaction of Nitroarenes with Aniline Anion Derivatives", Synthesis, No. 22, 2010, pp. 3865-3872.
Skerlj, R.T., et al., "Optimization of Potent Inhibitors of P. falciparum Dihydroorotate Dehydrogenase for the Treatment of Malaria", ACS Medicinal Chemistry Letters, vol. 2, No. 9, 2011, pp. 708-713.
Rondestvedt, C.S. Jr., "Synthesis of 4-Aminodiphenylamine and Its Relatives", The Journal of Organic Chemistry, vol. 42, No. 10, 1977, pp. 1786-1790.
Ibata, T., et al., "Nucleophilic Substitution Reaction of 2,3,5,6-Tetracloronitrobenzene with Primary and Secondary Amines Under High Pressure", Bulletin of the Chemical Society of Japan, vol. 67, No. 1, 1994, pp. 196-202.
Xu, Zhi-Bin, et al., "An Efficient and Fast Procedure for the Preparation of 2-Nitrophenylamines Under Microwave Conditions", Synlett No. 4, Dec. 3, 2003, pp. 564-566.
"Chloro derivatives of 2-Nitrodiphenylamine",Chem. Abdtr., vol. 43 col. 6175.
Chakrabarti, Jiban K., et al., "Synthesis and Pharmacological Evaluation of a Series of 4-Piperazinylpyrazolo [3,4-b]—and—[4,3-b][1,5] Benzodiazepines as Potential Anxiolytics" Journal of Medicinal Chemistry, vol. 32, No. 12, 1989, pp. 2573-2582.
PCT/JP2012/081492, International Preliminary Report on Patentability issued Jun. 17, 2014, eight(8) pages.
Borodkin, V-F.; "Synthesis of Chloro-Subsituted 2-Nitrodiphenylamines", Journal of Applied Chemistry; T. XXI, No. 10, pp. 1-13, 1948.

\* cited by examiner

DIPHENYLAMINE COMPOUNDS AND PRODUCTION METHOD THEREOF

TECHNICAL FIELD

The present invention relates to diphenylamine compounds and production method thereof. These diphenylamine compounds are useful, for example, as various organic compounds (e.g., biologically active organic compounds such as medicine and agricultural chemicals, functional pigments, electronic materials, or the like) or synthetic intermediates thereof by reason of diphenylamine.

BACKGROUND OF THE INVENTION

Diphenylamine compounds have widely been known as medicine and agricultural chemicals and intermediates thereof, and functional pigments, electronic materials and the like and intermediates thereof (see patent documents 1, 2 and 3).

Heretofore, it has been known that reaction of 2-chloronitrobenzene compound in which ortho position to nitro group is monosubstituted with chlorine, with aniline compound proceeds due to electron attracting characteristics of the nitro group (see non-patent document 1).

In order to increase the electron attracting characteristics of nitro group by resonance effect, better planarity to benzene ring is required, and when ortho position of nitro group is monosubstituted with chlorine, although the substitution doesn't entirely have adverse effects, there is a report that the reaction proceeds under a specific condition as described in non-patent document 1.

[Chemical Formula 1]

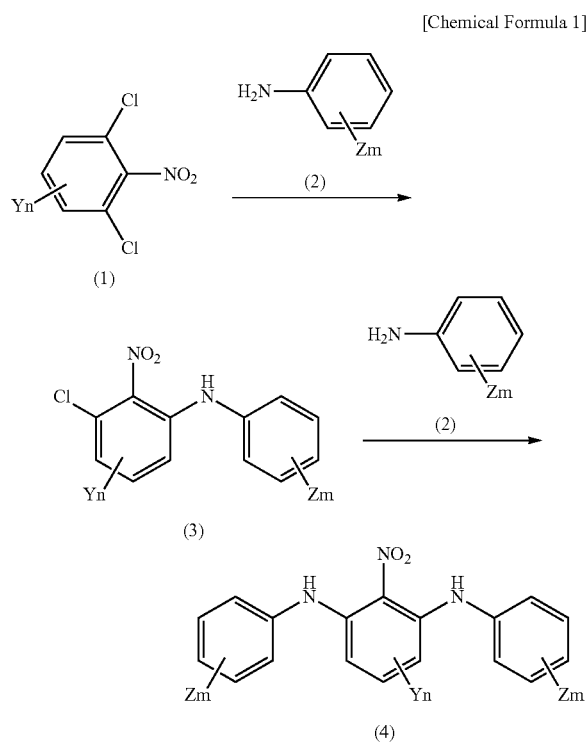

On the other hand, in the case of reaction between 2,6-dichloronitrobenzene compound in which ortho positions of nitro group are disubstituted with chlorine and aniline compound, the nitro group and benzene ring cannot take a coplanar structure due to the presence of chlorines on both sides of nitro group, thus the nitro group cannot increase its electron attracting characteristics by resonance effect, causing a problem of decrease in electrophilic reactivity.

For the purpose of compensating for such decline in electrophilic reactivity, known are methods to increase the electrophilic reactivity of 2,6-dichloronitrobenzene compound by introducing strong electron withdrawing groups (nitro group, trifluoromethyl group or cyano group, etc.) on the position of 3 to 5 of 2,6-dichloronitrobenzene compound, and methods to increase the nucleophilic reactivity of anilines by increasing acidity of amino group of aniline compound by introducing electron withdrawing groups into anilines and facilitating the reaction of aniline compound and base (see patent document 2). However, in these methods, it is necessary to introduce electron withdrawing group into 2,6-dichloronitrobenzene compounds and aniline compounds, that is, the methods have a defect that substituents are restricted.

As a method wherein the decrease of electrophilic reactivity is supplemented and substituents are not restricted, methods that are carried out under high temperature and/or high pressure are known (see patent document 3 and non-patent document 3, 4). However, when industrially implemented, the condition of high temperature and/or high pressure has disadvantages that many risks are involved and further special production facilities cost a great deal.

As a method that is carried out under high temperature and high pressure, a method described in patent document 3 is known. However, it is known that in particular, when nitro compounds are subjected to high temperature, they have an extremely high risk.

As a method that is carried out under high temperature, a method described in non-patent document 3 is also known. However, in addition to the above-mentioned defects, the yield of this method is relatively low.

Further, as shown in the above reaction formula, the condition of high temperature and/or high pressure may cause the formation of 2,6-di(phenylamino)nitrobenzene compound (di-form) as a by-product. On the other hand, in the case of 2-chloronitrobenzene compound in which ortho position to nitro group is monosubstituted with chlorine, the reaction can be conducted under a drastic condition such as high temperature and/or high pressure since there is no need to worry about occurring 2,6-di(phenylamino)nitrobenzene compound (di-form) as a by-product because the site to which the aniline compound can react is one. However, since 2,6-dichloronitrobenzene compound in which ortho positions of nitro group are disubstituted with chlorine has two reaction site, thus there is a concern about occurring 2,6-di(phenylamino)nitrobenzene compound (di-form) as a by-product, it is not preferable to conduct the reaction under a drastic condition such as high temperature and/or high pressure.

For example, as a method for conducting the reaction under high pressure, a method described in non-patent document 4 is known, but in addition to the above-mentioned defects, this method has disadvantages that 2,6-di(phenylamino)nitrobenzene compound (di-form) is produced as a by-product in considerable quantity, on top of low yield.

As a method wherein decrease of electrophilic reactivity is supplemented, substituents are not restricted and high temperature and high pressure can be avoided, a method using palladium catalyst is known (see non-patent document 2). However, use of expensive catalyst and reagent exemplified by these noble metal catalysts is not industrially preferable because of its high cost.

Furthermore under this condition, there is a disadvantage that 2,6-di(phenylamino)nitrobenzene compound (di-form) is formed in considerable quantity as a by-product, thus this is not a good method for producing diphenylamine compound which is 2-chloro-6-phenylaminonitrobenzene compound (mono-form) intended.

As another method wherein decrease of electrophilic reactivity is supplemented, substituents are not restricted and high temperature and high pressure can be avoided, a production method that makes the reaction easier by raising the acidity of amino group of aniline compounds by converting to formamide is known with respect to the example reaction of 2-chloronitrobenzene compound in which ortho position of nitro group is monosubstituted with chlorine and aniline compound (see non-patent document 5).

However, this method is not so convenient because the number of steps is increased, further there are disadvantages that it has a step which needs high temperature in addition to that the yield is relatively low.

As analogous methods to the above, a production method is known wherein an aniline compound is formamidated, and reacted with 2,6-dichloronitrobenzene compound, then deformylation is carried out (see patent document 1). However, it is confirmed that the yield is not so high in this method (see Comparison Example 9).

As furthermore method wherein decrease of electrophilic reactivity is supplemented, substituents are not restricted and high temperature and high pressure can be avoided, and as a reaction example using aminopyrazole compound instead of aniline compound in the reaction of 2-chloronitrobenzene compound and aniline compound, the condition is known that sodium hydride is used as base, tetrahydrofuran is used as solvent, and reaction is conducted at room temperature (see non-patent document 6). However, in the reaction of 2,6-dichloronitrobenzene compound and aniline compound, the intended compound couldn't be obtained under the condition described in non-patent document 6 (see Comparison Example 2).

PRIOR ART DOCUMENT

Patent Document patent document 1: WO2009/016841
patent document 2: JP1983-113151
patent document 3: US2003/0236260
non-patent document 1: Synlett., p. 564-566 (2003)
non-patent document 2: Eur. J. Org. Chem., p. 2243-2250 (2009)
non-patent document 3: Chem. Abstr., vol. 43, Column 6175 (1949)
non-patent document 4: Bull. Chem. Soc. Jpn., vol. 67, p. 196-202 (1994)
non-patent document 5: J. Org. Chem., vol. 42, p. 1786-1790 (1977)
non-patent document 6: J. Med. Chem., vol. 32, p. 2573-2582 (1989)

SUMMARY OF THE INVENTION

Problems to be Resolved by the Invention

The object of the present invention is to provide a method for producing diphenylamine compounds that is possible to solve one or more disadvantages and problems in the above-mentioned prior art.

The other object of the present invention is to provide a method for producing diphenylamine compounds wherein a condition of high temperature and/or high pressure is not needed that industrially involves danger and needs the use of specialized production facilities, and which enables the use of easily-available reagents under a mild condition without using expensive catalysts and reagents such as palladium catalysts, thus is inexpensive.

Further the other object of the present invention is to provide a method for producing diphenylamine compounds wherein the formation of 2,6-di(phenylamino)nitrobenzene compound (di-form) as a by-product can be suppressed, and a highly-pure target compound can be obtained with a high yield and efficiently (for example, conveniently on an industrial scale).

Furthermore the other object of the present invention is to provide diphenylamine compounds useful as medicine and agricultural chemicals and intermediates thereof, and functional pigments, electronic materials and the like and intermediates thereof.

Means of Solving the Problems

In consideration of the above-mentioned circumstances, the present inventors have intensively investigated about a method for producing diphenylamine compounds, and as the result, have unexpectedly found that the diphenylamine compounds represented by general formula (3) hereinafter described can be produced by reacting aniline compounds represented by general formula (2) hereinafter described with 2,6-dichloronitrobenzene compound represented by general formula (1) hereinafter described under the presence of base and ethers solvent, and based on this knowledge, finally completed the present invention.

That is, the present invention has resolved the above-mentioned problems by providing inventions described in the following items [1] to [26].

[1] A method for producing diphenylamine compounds represented by general formula (3):

[Chemical Formula 4]

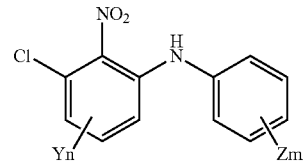

(3)

wherein, Y represents a halogen atom, C1-C4 alkyl group, C1-C4 alkoxy group or C1-C4 haloalkyl group, provided that halogen atom on para position of nitro group of 2,6-dichloronitrobenzene compound represented by general formula (1) is excluded; n represents an integer of 0 to 3; and when n is 2 or more, Y may be the same or different; Z represents a halogen atom, C1-C4 alkyl group, C1-C4 alkoxy group, C1-C4 haloalkyl group, C1-C4 alkoxy(C1-C4)alkyl group or C1-C4 alkoxycarbonyl group; m represents an integer of 0 to 5; and when m is 2 or more, Z may be the same or different; which is characterized by reacting aniline compounds represented by general formula (2):

[Chemical Formula 2]

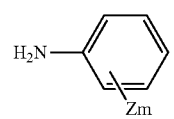

(2)

wherein, Z and m are as defined above; under the presence of base and ethers solvent, with 2,6-dichloronitrobenzene compound represented by general formula (1):

[Chemical Formula 3]

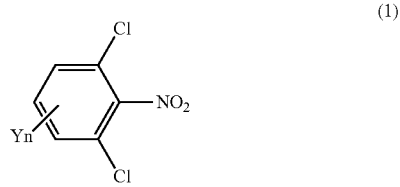

(1)

wherein, Y and n are as defined above.

[2] The method for producing diphenylamine compounds represented by general formula (3) according to the above-mentioned [1] wherein Y, Z, m and n have the same meaning as defined above, which is characterized by reacting aniline compounds represented by the above general formula (2) wherein Z and m have the same meaning as defined above, with base under the presence of ethers solvent, followed by reacting with 2,6-dichloronitrobenzene compound represented by general formula (1) wherein Y and n have the same meaning as defined above.

[3] The method for producing diphenylamine compounds according to the above-mentioned [1] or [2], wherein the ethers solvent is tetrahydrofuran.

[4] The method for producing diphenylamine compounds according to any one of the above-mentioned [1] to [3], wherein the base is alkali metal hydride or alkali metal.

[5] The method for producing diphenylamine compounds according to any one of the above-mentioned [1] to [3], wherein the base is sodium hydride or sodium metal.

[6] The method for producing diphenylamine compounds according to any one of the above-mentioned [1] to [3], wherein the base is sodium hydride.

[7] The method for producing diphenylamine compounds according to any one of the above-mentioned [2] to [6], wherein the reaction of aniline compound and base is carried out at the temperature of not less than 40° C. but not more than 90° C.

[8] The method for producing diphenylamine compounds according to any one of the above-mentioned [2] to [6], wherein the reaction of aniline compound and base is carried out at the temperature of not less than 50° C. but not more than 80° C.

[9] The method for producing diphenylamine compounds according to any one of the above-mentioned [1] to [7], wherein 2.0 moles or more of aniline compound represented by general formula (2) is used relative to 1 mole of 2,6-dichloronitrobenzene compound represented by general formula (1) and 2.0 equivalents or more of base is used relative to 1 mole of 2,6-dichloronitrobenzene compound represented by general formula (1).

[10] The method for producing diphenylamine compounds according to the above-mentioned [2], wherein the ethers solvent is tetrahydrofuran, the base is sodium hydride, the reaction of aniline compound and base is carried out at the temperature of not less than 40° C. but not more than 90° C., and 2.0 moles or more of aniline compound represented by general formula (2) is used relative to 1 mole of 2,6-dichloronitrobenzene compound represented by general formula (1) and 2.0 equivalents or more of base is used relative to 1 mole of 2,6-dichloronitrobenzene compound represented by general formula (1).

[11] The method for producing diphenylamine compounds according to any one of the above-mentioned [1] to [10], wherein Y is a halogen atom, C1-C4 alkyl group or C1-C4 alkoxy group, and Z is a halogen atom, C1-C4 alkyl group or C1-C4 alkoxy group.

[12] The method for producing diphenylamine compounds according to any one of the above-mentioned [1] to [10], wherein n is 0, Z is a halogen atom, C1-C4 alkyl group or C1-C4 alkoxy group, and m is an integer of 0 to 2.

[13] The method for producing diphenylamine compounds according to any one of the above-mentioned [1] to [10], wherein n is 0, Z is chlorine atom, methyl or methoxy, and m is an integer of 0 to 2.

[14] The method for producing diphenylamine compounds according to any one of the above-mentioned [1] to [10], wherein n is 0, and the aniline compound represented by general formula (2) is p-anisidine.

[15] A Diphenylamine compound represented by general formula (3):

[Chemical Formula 5]

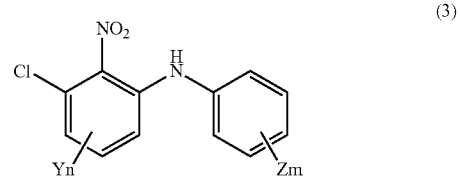

(3)

wherein, Y represents a halogen atom, C1-C4 alkyl group, C1-C4 alkoxy group or C1-C4 haloalkyl group, provided that halogen atom on para position of nitro group of diphenylamine compounds represented by general formula (3) is excluded; n represents an integer of 0 to 3; and when n is 2 or more, Y may be the same or different; Z represents a halogen atom, C1-C4 alkyl group, C1-C4 alkoxy group, C1-C4 haloalkyl group, C1-C4 alkoxy(C1-C4)alkyl group or C1-C4 alkoxycarbonyl group; m represents an integer of 0 to 5; and when m is 2 or more, Z may be the same or different; provided that compounds having CAS No. of 872296-37-2, 1172626-82-2, 1172626-81-1, 854873-67-9, 828921-30-8, 154595-53-6 or 854873-66-8 are excluded.

[16] The diphenylamine compounds according to the above-mentioned [15], wherein in general formula (3), n is 0, Z is a halogen atom, C1-C4 alkyl group or C1-C4 alkoxy group, and m is 1 or 2.

[17] The diphenylamine compounds according to the above-mentioned [16], wherein in general formula (3), Z is chlorine atom, methyl or methoxy.

[18] The diphenylamine compounds according to the above-mentioned [15], wherein in general formula (3), n is 0, Z is C1-C4 alkoxy group, C1-C4 haloalkyl group, C1-C4 alkoxy(C1-C4)alkyl group or C1-C4 alkoxycarbonyl group; and m represents an integer of 1 to 5.

[19] The diphenylamine compounds according to the above-mentioned [18], wherein Z is C1-C4 alkoxy group, and m represents an integer of 1 to 3.

[20] 3-Chloro-N-(4-methoxyphenyl)-2-nitroaniline.

[21] The method for producing diphenylamine compounds according to any one of the above-mentioned [1] to [14], wherein 2.0 moles or more but 6.0 moles or less of aniline compound represented by general formula (2) is used relative to 1 mole of 2,6-dichloronitrobenzene compound represented by general formula (1) and 2.0 equivalents or more but 6.0 equivalents or less of base is used relative to 1 mole of 2,6-dichloronitrobenzene compound represented by general formula (1).

[22] The method for producing diphenylamine compounds according to any one of the above-mentioned [1] to [14], wherein 2.0 moles or more but 4.0 moles or less of aniline compound represented by general formula (2) is used relative to 1 mole of 2,6-dichloronitrobenzene compound represented by general formula (1) and 2.0 equivalents or more but 4.0 equivalents or less of base is used relative to 1 mole of 2,6-dichloronitrobenzene compound represented by general formula (1).

[23] The method for producing diphenylamine compounds according to any one of the above-mentioned [1] to [14], [21] and [22], wherein the reaction of aniline compound and base is carried out at the temperature of not less than 50° C. and not more than 100° C.

[24] The method for producing diphenylamine compounds according to any one of the above-mentioned [1] to [14], [21] and [22], wherein the reaction of aniline compound and base is carried out at the temperature of not less than 50° C. and not more than 90° C.

[25] The method for producing diphenylamine compounds according to any one of the above-mentioned [1] to [14], [21] and [22], wherein the reaction of aniline compound and base is carried out at the temperature of not less than 45° C. and not more than 85° C.

[26] The method for producing diphenylamine compounds according to any one of the above-mentioned [1] to [7], [9] to [14], [21] and [22], wherein the reaction of aniline compound and base is carried out at the temperature of not less than 50° C. and not more than 80° C.

Effect of the Invention

By the method of the present invention, a novel industrial production method of diphenylamine compounds can be provided.

According to the method of the present invention, the targeted diphenylamine compounds can be produced without being affected by the problem of decrease in electrophilic reactivity supposed with regard to 2,6-dichloronitrobenzene compound of which both ortho positions of nitro group are disubstituted with chlorine, and at the same time, without the need to introduce electron attractive group into 2,6-dichloronitrobenzene compound and aniline compound which are raw materials, that is, without restriction of substituents.

Further, according to the method of the present invention, diphenylamine compounds can be produced with using industrially easily-available base and ethers solvent, that is, inexpensively without using an expensive catalyst and reagents.

Furthermore, according to the method of the present invention, diphenylamine compounds can be produced without requiring high temperature (for example, at a temperature of 100° C. or lower), and without requiring high pressure, that is, under a mild condition without industrially involving any danger and using specialized production facilities.

Furthermore, according to the method of the present invention, highly-pure diphenylamine compounds can conveniently be produced with a high yield and efficiently on an industrial scale without forming a by-product 2,6-di(phenylamino)nitrobenzene compound (di-form).

Therefore, the method of the present invention is environmentally-friendly, and has industrially a high utilization value.

Further, diphenylamine compounds which are novel compounds and useful as medicine and agricultural chemicals and intermediates thereof, and functional pigments, electronic materials and the like and intermediates thereof can be provided by the method of the present invention.

MODE FOR CARRYING OUT THE INVENTION

Hereinafter, the present invention will be described in detail.

(Production Method of Diphenylamine Compound)
The method of the present invention is a method for producing diphenylamine compounds represented by general formula (3) wherein aniline compound represented by general formula (2) is reacted with 2,6-dichloronitrobenzene compound represented by general formula (1) under the presence of base and ethers solvent.

The method of the present invention is a method for producing diphenylamine compounds represented by general formula (3) wherein, inter alia, aniline compound represented by general formula (2) is reacted with base under the presence of ethers solvent, followed by reacting with 2,6-dichloronitrobenzene compound represented by general formula (1).

The terms used in the specification are described below.
Halogen atom indicates fluorine atom, chlorine atom, bromine atom or iodine atom.

The C1-C4 alkyl group means a strait or branched chain alkyl group having 1 to 4 carbon atoms. The C1-C4 alkyl group includes, for example, methyl, ethyl, propyl, isopropyl, butyl, sec-butyl, isobutyl or tert-butyl.

The C1-C4 alkoxy group means a (C1-C4 alkyl)-O— group wherein the alkyl portion has the same meaning as the above-mentioned C1-C4 alkyl group. The C1-C4 alkoxy group includes, for example, methoxy, ethoxy, propoxy, isopropoxy, butoxy, sec-butoxy, isobutoxy or tert-butoxy.

The C1-C4 haloalkyl group means a strait or branched chain alkyl group having 1 to 4 carbon atoms which is substituted with the same or different 1 to 9 halogen atoms. The C1-C4 haloalkyl group includes, for example, fluoromethyl, chloromethyl, difluoromethyl, dichloromethyl, trifluoromethyl, trichloromethyl, chlorodifluoromethyl, bromodifluoromethyl, 1-fluoroethyl, 2-fluoroethyl, 1-chloroethyl, 2-chloroethyl, 2,2-difluoroethyl, 1,2-dichloroethyl, 2,2-dichloroethyl, 2-bromo-2-chloroethyl, 2,2,2-trifluoroethyl, 2,2,2-trichloroethyl, 1,1,2,2-tetrafluoroethyl, pentafluoroethyl, 1-chloro-1,2,2,2-tetrafluoroethyl, 2-chloro-1,1,2,2-tetrafluoroethyl, 3-fluoropropyl, 1-chloropropyl, 2-chloropropyl, 3-chloropropyl, 2-chloro-1-methylethyl, 2,3-difluoropropyl, 2,3-dichloropropyl, 3,3,3-trifluoropropyl, 3,3,3-trichloropropyl, 3-bromo-3,3-difluoropropyl, 3,3-dichloro-3-fluoropropyl, 2,2,3,3-tetrafluoropropyl, 2,2,2-trifluoro-1-fluoromethylethyl, 2,2,3,3,3-pentafluoropropyl, 1,2,2,2-tetrafluoro-1-fluoromethylethyl, heptafluoropropyl, 2,2,2-trifluoro-1-trifluoromethylethyl, 2,3-dichloro-1,1,2,3,3-pentafluoropropyl, 4-fluorobutyl, 4-chlorobutyl, 2-chloro-1,1-dimethylethyl, 2,2-dichloro-1,1-dimethylethyl, 4,4,4-trifluorobutyl, 2,3,4-trichlorobutyl, 4-chloro-4,4-difluorobutyl, 4-bromo-4,4-difluorobutyl, 4,4-dichloro-4-fluorobutyl, 3,3,3-trifluoro-1-methylpropyl, 3,3,3-trifluoro-2-methylpropyl, 2,2,2-trifluoro-1,1-dimethylethyl, 2,2,2-trichloro-1,1-dimethylethyl, 2-chloro-1-chloromethyl-2-methylethyl, 2,2,3,3,4,4-hexafluorobutyl, 2,2,3,4,4,4- hexafluorobutyl, 3,3-dichloro-4,4,4-trifluorobutyl, 3,4-dichloro-3,4,4-trifluorobutyl, 4-bromo-3,3,4,4-tetrafluorobutyl, 4-bromo-3-chloro-3,4,4-trifluorobutyl, 2,2,2-trifluoro-1-methyl-1-trifluoromethylethyl, 3,3,3-trifluoro-2-trifluoromethylpropyl, 2,2,3,3,4,4,4-heptafluorobutyl, 2,3,3,3-tetrafluoro-2-trifluoromethylpropyl, 1,1,2,2,3,3,4,4-octafluorobutyl, nonafluorobutyl, 4-chloro-1,1,2,2,3,3,4,4-octafluorobutyl or 2,2,2-trifluoro-1,1-di(trifluoromethyl)ethyl or the like. Preferable examples include fluoromethyl, difluoromethyl, trifluoromethyl, 1-fluoroethyl, 2-fluoroethyl, 2,2,2-trifluoroethyl, 1,1,2,2-tetrafluoroethyl, pentafluoroethyl, 3-fluoropropyl, 2,3-difluoropropyl, 3,3,3-trifluoropropyl, 2,2,3,3-tetrafluoropropyl, 2,2,3,3,3-pentafluoropropyl, heptafluoropropyl, 2,2,2-trifluoro-1-trifluoromethylethyl, 4-fluorobutyl, 4,4,4-trifluorobutyl, 3,3,3-trifluoro-1-methylpropyl, 3,3,3-trifluoro-2-methylpropyl, 2,2,2-trifluoro-1,1-dimethylethyl, 2,2,2-trifluoro-1-methyl-1-trifluoromethylethyl, 3,3,3-trifluoro-2-trifluoromethylpropyl, 2,2,3,3,4,4,4-heptafluorobutyl, 2,3,3,3-tetrafluoro-2-trifluoromethylpropyl, 1,1,2,2,3,3,4,4-octafluorobutyl, nonafluorobutyl or 2,2,2-trifluoro-1,1-di(trifluoromethyl)ethyl. More preferably, fluoromethyl, difluoromethyl, trifluoromethyl, 1-fluoroethyl, 2,2,2-trifluoroethyl, pentafluoroethyl, 3-fluoropropyl, 3,3,3-trifluoropropyl, 2,2,3,3,3-pentafluoropropyl, heptafluoropropyl, 2,2,2-trifluoro-1-trifluoromethylethyl, 4-fluorobutyl, 4,4,4-trifluorobutyl or nonafluorobutyl are exemplified.

The C1-C4 alkoxy(C1-C4)alkyl group means a C1-C4 alkoxy(C1-C4)alkyl group wherein the alkoxy portion has the same meaning as the above-mentioned C1-C4 alkoxy group, and the alkyl portion has the same meaning as the above-mentioned C1-C4 alkyl group. The C1-C4 alkoxy(C1-C4)alkyl group includes, for example, methoxymethyl, ethoxymethyl, propoxymethyl, isopropoxymethyl, butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-butoxyethyl, 1-(sec-butoxy)ethyl, 1-isobutoxyethyl, 1-(tert-butoxy)ethyl, 2-methoxyethyl, 2-ethoxyethyl, 2-propoxyethyl, 2-isopropoxyethyl, 2-butoxyethyl, 2-(sec-butoxy)ethyl, 2-isobutoxyethyl, 2-(tert-butoxy)ethyl, 3-methoxypropyl, 3-ethoxypropyl, 3-propoxypropyl, 3-isopropoxypropyl, 3-butoxypropyl, 3-(sec-butoxy)propyl, 3-isobutoxypropyl, 3-(tert-butoxy)propyl, 4-methoxybutyl, 4-ethoxybutyl, 4-propoxybutyl, 4-isopropoxybutyl, 4-butoxybutyl, 4-(sec-butoxy)butyl, 4-isobutyloxybutyl or 4-(tert-butoxy)butyl and the like.

The C1-C4 alkoxycarbonyl group means (C1-C4 alkoxy)-C(=O) group wherein the alkoxy portion has the same meaning as the above-mentioned C1-C4 alkoxy group. The C1-C4 alkoxycarbonyl group includes, for example, methoxycarbonyl, ethoxycarbonyl, propoxycarbonyl, isopropoxycarbonyl or tert-butoxycarbonyl and the like.

2,6-dichloronitrobenzene

First, raw material compounds represented by the above-mentioned general formula (1) to be used as raw materials of the method of the present invention will be described.

Y in general formula (1) indicates a halogen atom, C1-C4 alkyl group, C1-C4 alkoxy group or C1-C4 haloalkyl group, provided that halogen atom on para position of nitro group of 2,6-dichloronitrobenzene compound represented by general formula (1), that is, halogen atom on 4 position, is excluded; n represents an integer of 0 to 3; and when n is 2 or more, plural Y may be the same or different respectively.

Those having halogen atom on para position of nitro group of 2,6-dichloronitrobenzene compound represented by general formula (1) are excluded from the scope of the present invention because in case that there exists a halogen atom on para position of nitro group of 2,6-dichloronitrobenzene compound represented by general formula (1), the said halogen atom on 4 position becomes involved in the reaction and therefore it is difficult to obtain the target compound with a good yield.

The 2,6-dichloronitrobenzene compounds represented by general formula (1) include specifically, for example,
2,6-dichloronitrobenzene,
2,6-dichloro-3-fluoronitrobenzene,
2,3,6-trichloronitrobenzene,
3-bromo-2,6-dichloronitrobenzene,
2,6-dichloro-3-iodonitrobenzene,
2,3,5,6-tetrachloronitrobenzene,
2,6-dichloro-4-methylnitrobenzene,
2,6-dichloro-3-methylnitrobenzene,
2,6-dichloro-4-ethylnitrobenzene,
2,6-dichloro-3-ethylnitrobenzene,
2,6-dichloro-4-propylnitrobenzene,
2,6-dichloro-3-propylnitrobenzene,
2,6-dichloro-4-butylnitrobenzene,
2,6-dichloro-3-butylnitrobenzene,
2,6-dichloro-4-(tert-butyl)nitrobenzene,
2,6-dichloro-3-(tert-butyl)nitrobenzene,
2,6-dichloro-4-methoxynitrobenzene,
2,6-dichloro-3-methoxynitrobenzene,
2,6-dichloro-4-ethoxynitrobenzene,
2,6-dichloro-3-ethoxynitrobenzene,
2,6-dichloro-4-propoxynitrobenzene,
2,6-dichloro-3-propoxynitrobenzene,
2,6-dichloro-4-butoxynitrobenzene,
2,6-dichloro-3-butoxynitrobenzene,
2,6-dichloro-4-(tert-butoxy)nitrobenzene,
2,6-dichloro-3-(tert-butoxy)nitrobenzene,
2,6-dichloro-4-trifluoromethylnitrobenzene,
2,6-dichloro-3-trifluoromethylnitrobenzene,
2,6-dichloro-4-(2,2,3,3,4,4,4-heptafluorobutyl)nitrobenzene,
2,6-dichloro-3-(2,2,3,3,4,4,4-heptafluorobutyl)nitrobenzene and the like.

The 2,6-dichloronitrobenzene compounds represented by general formula (1) are a known compound, or a compound that can be produced from a known compound by known methods.

(Aniline Compound)

Next, raw material compounds represented by the above-mentioned general formula (2) to be used as raw materials of the method of the present invention will be described.

Z in general formula (2) represents a halogen atom, C1-C4 alkyl group, C1-C4 alkoxy group, C1-C4 haloalkyl group, C1-C4 alkoxy(C1-C4)alkyl group or C1-C4 alkoxycarbonyl group; m represents an integer of 0 to 5; and when m is 2 or more, plural Z may be the same or different respectively.

The aniline compounds represented by general formula (2) include specifically, for example,
aniline,
2-chloroaniline,
3-chloroaniline,
4-chloroaniline,
2-fluoroaniline,
3-fluoroaniline,
4-fluoroaniline,
4-bromoaniline, 4-iodoaniline,
2-methylaniline,
3-methylaniline,
4-ethylaniline,
4-propylaniline,
4-butylaniline,
4-(tert-butyl)aniline,
2-methoxyaniline,
3-methoxyaniline,
4-methoxyaniline,
4-ethoxyaniline,
4-propoxyaniline,
4-butoxyaniline,
4-(sec-butoxy)aniline,
4-isobutoxyaniline,
4-(tert-butoxy)aniline,
2-trifluoromethylaniline,
3-trifluoromethylaniline,
4-trifluoromethylaniline,
4-(2,2,2-trifluoroethyl)aniline,
4-(3,3,3-trifluoropropyl)aniline,
4-(3,3,3,2,2-pentafluoropropyl)aniline,
2-methoxymethylaniline,
3-methoxymethylaniline,
4-methoxymethylaniline,
4-(2-methoxyethyl)aniline,
4-(3-methoxypropyl)aniline,
4-(4-methoxybutyl)aniline,
4-ethoxymethylaniline,
4-butoxymethylaniline,
2-methoxycarbonylaniline,
3-methoxycarbonylaniline,
4-methoxycarbonylaniline,
4-ethoxycarbonylaniline,
4-propoxycarbonylaniline,
4-butoxycarbonylaniline,
4-(tert-butoxycarbonyl)aniline,
2,4-dichloroaniline,
3,4-dichloroaniline,
3,5-dichloroaniline,
2,5-dichloroaniline,
2,6-dichloroaniline,
2-fluoro-4-chloroaniline,
2,4-dimethylaniline,
3,4-dimethylaniline,
3,5-dimethylaniline,
2,6-dimethylaniline,
2,4-dimethoxyaniline,
3,4-dimethoxyaniline,
3,5-dimethoxyaniline,
2,6-dimethoxyaniline,
3,4,5-trimethoxyaniline,
2-fluoro-4-methylaniline,
3-fluoro-4-methylaniline,
4-fluoro-3-methylaniline,
2-chloro-4-methylaniline,
3-chloro-4-methylaniline,
4-chloro-3-methylaniline,
3-fluoro-4-methoxyaniline,
4-fluoro-3-methoxyaniline,
3-chloro-4-methoxyaniline,
4-chloro-3-methoxyaniline,
3-methyl-4-methoxyaniline,
4-methyl-3-methoxyaniline and the like.

The aniline compounds represented by general formula (2) are a known compound, or a compound that can be produced from a known compound by known methods.

(Amount of Aniline Compound Used)

The using molar ratio of aniline compound represented by general formula (2) in the method of the present invention can be exemplified by, from a viewpoint of yield and the like, usually 1.0 mole or more, preferably 2.0 mole or more of aniline compound represented by general formula (2) relative to 1 mole of 2,6-dichloronitrobenzene compounds represented by general formula (1) (raw material compound). Further, from an economic perspective and the like, the using molar ratio of aniline compound represented by general formula (2) can be exemplified by usually 10.0 mole or less, preferably 6.0 mole or less, more preferably 4.0 mole or less of aniline compound represented by general formula (2) relative to 1 mole of 2,6-dichloronitrobenzene compounds represented by general formula (1) (raw material compound). Thus, regarding the using molar ratio of aniline compound represented by general formula (2), the scope of aniline compound represented by general formula (2) relative to 1 mole of 2,6-dichloronitrobenzene compounds represented by general formula (1) (raw material compound) can be exemplified by, usually 1.0 to 10.0 mole, preferably 1.0 to 6.0 mole, more preferably 2.0 to 6.0 mole, furthermore preferably 2.0 to 4.0 mole.

(Diphenylamine Compound)

Further, the diphenylamine compounds represented by general formula (3) that can be obtained in the method of the present invention will be described.

In general formula (3), Y, Z, m and n have the same meaning as defined above. That is, Y represents a halogen atom, C1-C4 alkyl group, C1-C4 alkoxy group or C1-C4 haloalkyl group, provided that halogen atom on para position of nitro group of diphenylamine compounds represented by general formula (3) is excluded; n represents an integer of 0 to 3; and when n is 2 or more, plural Y may be the same or different respectively; Z represents a halogen atom, C1-C4 alkyl group, C1-C4 alkoxy group, C1-C4 haloalkyl group, C1-C4 alkoxy(C1-C4)alkyl group or C1-C4 alkoxycarbonyl group; m represents an integer of 0 to 5; and when m is 2 or more, plural Z may be the same or different respectively. In addition, as shown in the following, the compounds having CAS No. of 872296-37-2, 1172626-82-2, 1172626-81-1, 854873-67-9, 828921-30-8, 154595-53-6 or 854873-66-8 are known publicly, thus are excluded from the scope of diphenylamine compounds of the present invention.

The preferred compounds having general formula (3) are diphenylamine compounds wherein n is 0, Z is a halogen atom, C1-C4 alkyl group or C1-C4 alkoxy group and m is 1 or 2 (when m is 2, Z may be the same or different), and the more preferred compounds are diphenylamine compounds wherein n is 0, Z is chlorine atom, methyl or methoxy, and m is 1 or 2 (when m is 2, Z may be the same or different).

The preferred compounds having general formula (3) are diphenylamine compounds wherein n is 0, Z is C1-C4 alkoxy group, C1-C4 haloalkyl group, C1-C4 alkoxy(C1-C4)alkyl group or C1-C4 alkoxycarbonyl group, and m represents an integer of 1 to 5 (when m is 2 or more, Z may be the same or different), and the more preferred compounds are diphenylamine compounds wherein n is 0, Z is C1-C4 alkoxy group, and m represents an integer of 1 to 3 (when m is 2 or more, Z may be the same or different).

The preferred compounds having general formula (3) are those wherein Z is C1-C4 alkoxy group, more preferably methoxy.

Particularly preferred compound having general formula (3) is 3-chloro-N-(4-methoxyphenyl)-2-nitroaniline.

The diphenylamine compounds represented by general formula (3) that can be produced by the method of the present invention include specifically, for example,
3-chloro-N-(4-chlorophenyl)-2-nitroaniline,
3-chloro-N-(3-chlorophenyl)-2-nitroaniline,
3-chloro-N-(2-chlorophenyl)-2-nitroaniline,
3-chloro-N-(4-fluorophenyl)-2-nitroaniline,
N-(4-bromophenyl)-3-chloro-2-nitroaniline,
3-chloro-N-(4-iodophenyl)-2-nitroaniline,
3-chloro-N-(4-methylphenyl)-2-nitroaniline,
3-chloro-N-(3-methylphenyl)-2-nitroaniline,
3-chloro-N-(2-methylphenyl)-2-nitroaniline,
N-[4-(tert-butyl)phenyl]-3-chloro-2-nitroaniline,
3-chloro-N-(4-methoxyphenyl)-2-nitroaniline,
3-chloro-N-(3-methoxyphenyl)-2-nitroaniline,
3-chloro-N-(2-methoxyphenyl)-2-nitroaniline,
N-[4-(tert-butoxy)phenyl]-3-chloro-2-nitroaniline,
3-chloro-2-nitro-N-(4-trifluoromethylphenyl)aniline,
3-chloro-N-[4-(2,2,3,3,4,4,4-heptafluorobutyl)phenyl]-2-nitroaniline,
3-chloro-N-(4-methoxycarbonylphenyl)-2-nitroaniline,
N-[4-(tert-butoxycarbonyl)phenyl]-3-chloro-2-nitroaniline,
3-chloro-N-(4-methoxymethylphenyl)-2-nitroaniline,
3-chloro-N-[4-(4-methoxybutyl)phenyl]-2-nitroaniline,
N-(4-butoxymethylphenyl)-3-chloro-2-nitroaniline,
3-chloro-N-(3-chloro-4-methoxyphenyl)-2-nitroaniline,
3-chloro-4-fluoro-N-(4-methoxyphenyl)-2-nitroaniline,
3,4-dichloro-N-(4-methoxyphenyl)-2-nitroaniline,
4-bromo-3-chloro-N-(4-methoxyphenyl)-2-nitroaniline,
3-chloro-4-iodo-N-(4-methoxyphenyl)-2-nitroaniline,
3-chloro-N-(4-methoxyphenyl)-5-methyl-2-nitroaniline,
5-(tert-butyl)-3-chloro-N-(4-methoxyphenyl)-2-nitroaniline,
3-chloro-5-methoxy-N-(4-methoxyphenyl)-2-nitroaniline,
5-(tert-butoxy)-3-chloro-N-(4-methoxyphenyl)-2-nitroaniline,
3-chloro-N-(4-methoxyphenyl)-2-nitro-5-trifluoromethylaniline,
3-chloro-5-(2,2,3,3,4,4,4-heptafluorobutyl)-N-(4-methoxyphenyl)-2-nitroaniline and the like.

Production Method of Agricultural Chemicals Using 3-chloro-N-(4-methoxyphenyl)-2-nitroaniline By using 3-chloro-N-(4-methoxyphenyl)-2-nitroaniline), a convenient and economical synthetic method of 5-chloro-3-(2-hydroxy-6-oxo-1-cyclohexenecarbonyl)-1-(4-methoxyphenyl)quinoxaline-2-(1H)-one useful as agricultural chemicals can be provided according to the method described in Examples 19 to 23.

(Base)

Next, the base used in the method of the present invention is described. As long as any reaction in the method of the present invention described below will proceed, any base can be used. The bases used in the method of the present invention include, for example, alkali metal hydrides or alkali metals. Preferably alkali metal hydrides are exemplified.

(Alkali Metal Hydrides)

The alkali metal hydrides include, for example, sodium hydride or potassium hydride. Preferably sodium hydride is exemplified.

(Alkali Metal)

As alkali metals, for example, sodium metal or potassium metal are exemplified. Preferably sodium metal is exemplified.

As the base used in the method of the present invention, from the viewpoint of availability, convenience of handling, or cost etc., for example, preferably alkali metal hydrides or alkali metals, more preferably sodium hydride or sodium metal, furthermore preferably sodium hydride can be exemplified.

Either of the bases mentioned-above may be used alone, or with mixing 2 kinds or more of the bases at an arbitrary rate.

(Amount of Base Used)

As the amount of base to be used in the method of the present invention, the scope of preferably 1 equivalent or more, more preferably 1.0 to 10.0 equivalents, furthermore preferably 2.0 to 6.0 equivalents, particularly preferably 2.0 to 4.0 equivalents relative to 1 mole of 2,6-dichloronitrobenzene compound represented by general formula (1) can be exemplified.

(Ethers Solvent)

Further, the ethers solvent to be used in the method of the present invention is described. In the method of the present invention, ethers are used as a solvent.

(Ethers)

As long as any reaction in the method of the present invention described below will proceed, any ether can be used. Examples of the ethers include, for example, tetrahydrofuran (THF), 2-methyltetrahydrofuran, cyclopentyl methyl ether (CPME), methyl-tert-butyl ether, diethyl ether, diisopropyl ether, di-tert-butyl ether, diphenyl ether, 1,2-dimethoxyethane (DME), diglyme, triglyme, 1,4-dioxane or the like, and preferably tetrahydrofuran, 2-methyltetrahydrofuran or cyclopentyl methyl ether is exemplified, and more preferably tetrahydrofuran is exemplified.

(Using Method of Ethers; Alone or Mixing Ethers)

As ethers solvent, one of the ethers mentioned-above can be used alone, or can be used with mixing 2 or more of the ethers mentioned-above at an arbitrary rate.

(Amount of Ethers Solvent to be Used)

As the amount of ethers solvent to be used, the scope of usually 10.0 L or less, preferably 0.01 to 10.0 L, more preferably 0.01 to 5.0 L, furthermore preferably 0.1 to 5.0 L, particularly preferably 0.2 to 3.0 L relative to 1 mole of 2,6-dichloronitrobenzene compound represented by general formula (1) can be exemplified.

(Mixed Solvent)

The ethers solvent can be used alone, or can be used by mixing with 1 or more solvents other than ethers solvent.

(Other Solvents Other than Ethers Solvent)

The other solvents used for the mixed solvent may be any solvent that doesn't have a harmful effect on the method of the present invention, for example, such as those that either reaction in the method of the present invention mentioned below is not inhibited. Examples of the other solvents used for the mixed solvent include, for example, aromatic hydrocarbons such as benzene, toluene, xylene, chlorobenzene, dichlorobenzene or nitrobenzene etc., or ketones such as acetone, methyl ethyl ketone, methyl isopropyl ketone or methyl isobutyl ketone (MIBK) etc., preferably include aromatic hydrocarbons such as benzene, toluene, xylene, chlorobenzene, dichlorobenzene or nitrobenzene etc., more preferably include toluene, xylene or chlorobenzene, furthermore preferably include toluene or xylene, and particularly preferably include toluene, but are not limited to these.

(Used Amount of the Other Solvent Other than Ethers Solvent)

When the other solvent to be used for the mixed solvent is used, amount of the other solvent used may be any scope that doesn't have a harmful effect on the method of the present invention, for example, such as those that either reaction in the method of the present invention mentioned below is not inhibited. As the amount of the other solvent used, the scope of usually 10.0 L or less, preferably 0.01 to 10.0 L, more preferably 0.01 to 5.0 L, furthermore preferably 0.1 to 5.0 L, and particularly preferably 0.2 to 3.0 L relative to 1 mole of 2,6-dichloronitrobenzene compound represented by general formula (1) can be exemplified, but not limited to these.

(Ratio in Mixed Solvent)

When the other solvent to be used for the mixed solvent is used, the mixing ratio of the other solvent to ethers solvent in the mixed solvent may be any scope that doesn't have a harmful effect on the method of the present invention, for example, such as those that either reaction in the method of the present invention mentioned below is not inhibited.

The mixing ratio of the other solvent to ethers solvent in the mixed solvent is the value represented by the following formula.

mixing ratio(vol/vol)=other solvent/ethers solvent

As the mixing ratio represented by the above formula, the scope of usually 10 or less, preferably 0.1 or more and 10 or less, more preferably 0.2 or more and 5 or less, furthermore preferably 0.25 or more and 4 or less can be exemplified, but not limited to these.

(Reaction Temperature of Aniline Compound with Base)

As the reaction temperature of aniline compound represented by general formula (2) with base, from the viewpoint of reactivity, inhibition of by-products, economy and the like, the scope of usually not less than 40° C. and not more than 100° C., preferably not less than 40° C. and not more than 90° C., more preferably not less than 45° C. and not more than 85° C., and furthermore preferably not less than 50° C. and not more than 80° C. can be exemplified, but not limited to these.

(Reaction Time of Aniline Compound with Base)

The reaction time of aniline compound represented by general formula (2) with base is not particularly restricted, but from the viewpoint of inhibition of by-products, economy and the like, the scope of usually 0.1 hr to 48 hrs, preferably 0.1 hr to 30 hrs, more preferably 0.1 hr to 24 hrs, furthermore preferably 0.1 hr to 12 hrs, and particularly preferably 0.1 hr to 8 hrs can be exemplified.

(Temperature of Reaction with 2,6-dichloronitrobenzene Compound after Reacting aniline Compound with Base)

As the temperature of reaction with 2,6-dichloronitrobenzene compound represented by general formula (1) after the reaction of aniline compound represented by general formula (2) with base, from the viewpoint of reactivity, inhibition of by-products, economy and the like, the scope of usually not less than −80° C. and not more than 100° C., preferably not less than −40° C. and not more than 50° C., more preferably not less than −35° C. and not more than 45° C., furthermore preferably not less than −30° C. and not more than 40° C., and particularly preferably not less than −30° C. and not more than 35° C. can be exemplified, but not limited to these.

(Time of Reaction with 2,6-dichloronitrobenzene Compound after Reacting Aniline Compound with Base)

The time for reacting with 2,6-dichloronitrobenzene compound represented by general formula (1) after reacting aniline compound represented by general formula (2) with base is not particularly restricted, but from the viewpoint of inhibition of by-products, economy and the like, the scope of usually 0.1 hr to 48 hrs, preferably 0.1 hr to 30 hrs, more preferably 0.1 hr to 24 hrs, furthermore preferably 0.1 hr to 12 hrs, and particularly preferably 0.2 hr to 8 hrs can be exemplified.

According to the method of the present invention, diphenylamine compounds represented by general formula (3) can be produced with a high yield under a mild condition without using specialized reaction apparatus. The diphenylamine compounds represented by general formula (3) obtained are useful as medicine, agricultural chemicals, functional pigments, electronic materials and the like and synthetic intermediates thereof.

(Yield)

In the present invention, yield of the targeted product is preferably 70% or more, more preferably 75 to 90%, and furthermore preferably 77 to 95% (particularly preferably 79 to 95%).

This yield can be calculated from the mole number of target diphenylamine compound obtained relative to the mole number of raw material 2,6-dichloronitrobenzene compound represented by general formula (1). That is, yield in the present invention is represented by the following formula.

Yield (%)=100×[(mole number of target compound obtained)/(mole number of raw material of general formula (1))]

In Examples 1 to 18 described below, 1 mole of target diphenylamine compound can theoretically be produced from 1 mole of raw material 2,6-dichloronitrobenzene compound of general formula (1). Thus, based on this theoretical value, practical yield can be calculated.

EXAMPLES

The present invention is described in detail with reference to Examples, but the present invention is not limited to these Examples. Herein, room temperature indicates 10° C. to 35° C. In addition, for the determination of each physical property in Examples and Comparison Examples, following instruments were used. 1H nuclear magnetic resonance spectrum (1H-NMR): JEOL JMN-Lambda300, JEOL JMN-Lambda-400 (manufactured by JEOL Ltd.), internal standard substance: tetramethylsilane. Mass spectrometric analysis: HP6890 (FID) (manufactured by Agilent inc.). Melting point: Yanaco Mp-500V (manufactured by Anatec Yanaco).

Example 1

Production of 3-chloro-N-(4-methoxyphenyl)-2-nitroaniline 1.00 g (26 mmol) of sodium hydride (purity 62.3%) was suspended in THF 10 ml, and p-anisidine 2.95 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained reaction solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. The resulting crude product was purified by column chromatography to give the targeted 3-chloro-N-(4-methoxyphenyl)-2-nitroaniline 2.32 g as red crystal (yield 80%).

Melting point: 73-74° C.

$^1$H-NMR (300 MHz, CDCl$_3$) δ: 7.30 (s, 1H), 6.83-7.20 (m, 7H), 3.83 (s, 3H) ppm Example 2

Production of 3-chloro-N-(4-methoxyphenyl)-2-nitroaniline 1.00 g (26 mmol) of sodium hydride (purity 62.3%) was suspended in THF 10 ml, and p-anisidine 2.95 g (24 mmol) was added at 70° C. under a nitrogen gas stream, followed by stirring at the same temperature for 2 hours. The resulting reaction solution was cooled to −20° C., and a solution of 2,6-dichloronitrobenzene 2.0 g (10 mmol) in THF 15 ml was added dropwise thereto with keeping the inner temperature from exceeding −20° C. After finishing the dropping, the solution was stirred at −20~-25° C. for 30 minutes, then warmed to room temperature. The obtained reaction solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. The resulting crude product was purified by column chromatography to give the targeted 3-chloro-N-(4-methoxyphenyl)-2-nitroaniline 2.31 g as red crystal (yield 79%).

Example 3

Production of 3-chloro-N-(4-methoxyphenyl)-2-nitroaniline 1.40 g (36 mmol) of sodium hydride (purity 62.3%) was suspended in THF 10 ml, and p-anisidine 4.23 g (34 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. The resulting crude product was purified by column chromatography to give the targeted 3-chloro-N-(4-methoxyphenyl)-2-nitroaniline 2.47 g as red crystal (yield 85%).

Example 4

Production of 3-chloro-N-(4-methoxyphenyl)-2-nitroaniline 1.40 g (36 mmol) of sodium hydride (purity 62.3%) was suspended in THF 10 ml, and p-anisidine 4.23 g (34 mmol) was added at 70° C. under a nitrogen gas stream, followed by stirring at the same temperature for 2 hours. The resulting reaction solution was cooled to −20° C., and a solution of 2,6-dichloronitrobenzene 2.0 g (10 mmol) in THF 15 ml was added dropwise thereto with keeping the inner temperature from exceeding −20° C. After finishing the dropping, the solution was stirred at −20~-25° C. for 30 minutes, then warmed to room temperature. The obtained reaction solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. The resulting crude product was purified by column chromatography to give the targeted 3-chloro-N-(4-methoxyphenyl)-2-nitroaniline 2.40 g as red crystal (yield 83%).

Example 5

Production of 3-chloro-N-(4-methoxyphenyl)-2-nitroaniline 9.30 g (250 mmol) of sodium hydride (purity 64.5%) was suspended in THF 48.2 mL, and a solution of p-anisidine 28.3 g (230 mmol) in THF 32.0 mL was added dropwise at 60° C. under a nitrogen gas stream, followed by stirring at the same temperature for 1 hour. Then, after cooling to room temperature, the resulting reaction solution was added dropwise to a solution of 2,6-dichloronitrobenzene 19.2 g (100 mmol) in toluene 117.8 mL at 11~15° C. After finishing the dropping, the solution was stirred at the same temperature for 1 hour, and the obtained solution was poured into water 64.8 mL and concentrated hydrochloric acid 52.1 mL. After the organic phase obtained was washed further with water 22.5 mL, THF was distilled away to give 65.6 g of toluene solution of the targeted 3-chloro-N-(4-methoxyphenyl)-2-nitroaniline as a red solution. This toluene solution was analyzed with HPLC absolute calibration curve method, with the result that the yield of 3-chloro-N-(4-methoxyphenyl)-2-nitroaniline was 87%.

Example 6

Production of 3-chloro-N-(4-methoxyphenyl)-2-nitroaniline 0.48 g (13 mmol) of sodium hydride (purity 62.3%) was suspended in THF 10 ml, and p-anisidine 1.41 g (11 mmol) was added at 70° C. under a nitrogen gas stream, followed by stirring at the same temperature for 2 hours. After cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. The resulting crude product was purified by column chromatography to give the targeted 3-chloro-N-(4-methoxyphenyl)-2-nitroaniline 0.70 g as red crystal (yield 24%).

Example 7

Production of 3-chloro-N-(4-methoxyphenyl)-2-nitroaniline 0.48 g (13 mmol) of sodium hydride (purity 62.3%) was suspended in THF 10 ml, and p-anisidine 1.41 g (11 mmol) was added at 70° C. under a nitrogen gas stream, followed by stirring at the same temperature for 2 hours. The resulting reaction solution was cooled to −20° C., and a solution of 2,6-dichloronitrobenzene 2.0 g (10 mmol) in THF 15 ml was added dropwise thereto with keeping the inner temperature from exceeding −20° C. After finishing the dropping, the solution was stirred at −20~−25° C. for 30 minutes, then warmed to room temperature. The obtained reaction solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. The resulting crude product was purified by column chromatography to give the targeted 3-chloro-N-(4-methoxyphenyl)-2-nitroaniline 0.88 g as red crystal (yield 30%).

Example 8

Production of 3-chloro-N-(4-methoxyphenyl)-2-nitroaniline 1.00 g (26 mmol) of sodium hydride (purity 62.3%) was suspended in CPME (cyclopentyl methyl ether) 10 ml, and p-anisidine 2.95 g (24 mmol) was added at 70° C. under a nitrogen gas stream, followed by stirring at the same temperature for 2 hours. The resulting reaction solution was cooled to −20° C., and a solution of 2,6-dichloronitrobenzene 2.0 g (10 mmol) in CPME 15 ml was added dropwise thereto with keeping the inner temperature from exceeding −20° C. After finishing the dropping, the solution was stirred at −20~−25° C. for 30 minutes, then warmed to room temperature. The obtained reaction solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. The resulting crude product was purified by column chromatography to give the targeted 3-chloro-N-(4-methoxyphenyl)-2-nitroaniline 1.33 g as red crystal (yield 46%).

Example 9

Production of 3-chloro-N-(4-methoxyphenyl)-2-nitroaniline 1.00 g (26 mmol) of sodium hydride (purity 62.3%) was suspended in 2-methyltetrahydrofuran 10 ml, and p-anisidine 2.95 g (24 mmol) was added at 70° C. under a nitrogen gas stream, followed by stirring at the same temperature for 2 hours. The resulting reaction solution was cooled to −20° C., and a solution of 2,6-dichloronitrobenzene 2.0 g (10 mmol) in 2-methyltetrahydrofuran 15 ml was added dropwise thereto with keeping the inner temperature from exceeding −20° C. After finishing the dropping, the solution was stirred at −20~−25° C. for 30 minutes, then warmed to room temperature. The obtained reaction solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. The resulting crude product was purified by column chromatography to give the targeted 3-chloro-N-(4-methoxyphenyl)-2-nitroaniline 1.01 g as red crystal, which was contaminated with impurity (purity of the target compound by gas chromatography 90%).

Example 10

Production of 3-chloro-N-(3-methoxyphenyl)-2-nitroaniline 1.00 g (26 mmol) of sodium hydride (purity 62.3%) was suspended in THF 10 ml, and m-anisidine 2.95 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(3-methoxyphenyl)-2-nitroaniline 2.24 g as red crystal (yield 77%).

$^1$H-NMR (300 MHz, CDCl$_3$) δ: 7.35-7.46 (m, 2H), 7.20-7.28 (m, 2H), 6.93-6.96 (m, 1H), 6.69-6.74 (m, 3H), 3.80 (s, 3H) ppm Example 11

Production of 3-chloro-N-(2-methoxyphenyl)-2-nitroaniline 1.00 g (26 mmol) of sodium hydride (purity 62.3%) was suspended in THF 10 ml, and o-anisidine 2.95 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(2-methoxyphenyl)-2-nitroaniline 2.22 g as red liquid (yield 77%).

$^1$H-NMR (300 MHz, CDCl$_3$) δ: 6.93-7.46 (m, 8H), 3.88 (s, 3H) ppm

Example 12

Production of 3-chloro-N-(4-methylphenyl)-2-nitroaniline 1.00 g (26 mmol) of sodium hydride (purity 62.3%) was suspended in THF 10 ml, and p-toluidine 2.57 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(4-methylphenyl)-2-nitroaniline 2.33 g as red liquid, which was contaminated with raw material and impurity (purity of the target compound by gas chromatography 66%).

$^1$H-NMR (300 MHz, CDCl$_3$) δ: 7.04-7.46 (m, 7H), 6.87-6.89 (m, 1H), 2.35 (s, 3H) ppm

Example 13

Production of 3-chloro-N-(3-methylphenyl)-2-nitroaniline 1.00 g (26 mmol) of sodium hydride (purity 62.3%) was suspended in THF 10 ml, and m-toluidine 2.57 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(3-methylphenyl)-2-nitroaniline 2.24 g as red liquid, which was contaminated with raw material and impurity (purity of the target compound by gas chromatography 81%).

$^1$H-NMR (300 MHz, CDCl$_3$) δ: 7.17-7.47 (m, 4H), 6.90-6.97 (m, 4H), 2.34 (s, 3H) ppm

Example 14

Production of 3-chloro-N-(2-methylphenyl)-2-nitroaniline 1.00 g (26 mmol) of sodium hydride (purity 62.3%) was suspended in THF 10 ml, and o-toluidine 2.57 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(2-methylphenyl)-2-nitroaniline 1.85 g as red liquid, which was contaminated with raw material and impurity (purity of the target compound by gas chromatography 82%).

$^1$H-NMR (300 MHz, CDCl$_3$) δ: 7.11-7.47 (m, 6H), 6.78-6.89 (m, 2H), 2.24 (s, 3H) ppm

Example 15

Production of 3-chloro-N-(4-chlorophenyl)-2-nitroaniline 1.00 g (26 mmol) of sodium hydride (purity 62.3%) was suspended in THF 10 ml, and p-chloroaniline 2.95 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(4-chlorophenyl)-2-nitroaniline 2.58 g as red crystal (yield 87%).

$^1$H-NMR (300 MHz, CDCl$_3$) δ: 7.00-7.46 (m, 8H) ppm

Example 16

Production of 3-chloro-N-(3-chlorophenyl)-2-nitroaniline 1.00 g (26 mmol) of sodium hydride (purity 62.3%) was suspended in THF 10 ml, and m-chloroaniline 2.95 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(3-chlorophenyl)-2-nitroaniline 2.64 g as red brown crystal (yield 89%).

$^1$H-NMR (300 MHz, CDCl$_3$) δ: 6.99-7.45 (m, 8H) ppm

Example 17

Production of 3-chloro-N-(2-chlorophenyl)-2-nitroaniline 1.00 g (26 mmol) of sodium hydride (purity 62.3%) was suspended in THF 10 ml, and o-chloroaniline 2.95 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(3-chlorophenyl)-2-nitroaniline 2.51 g as red brown crystal (yield 85%).

$^1$H-NMR (300 MHz, CDCl$_3$) δ: 7.02-7.45 (m, 8H) ppm

Example 18

Production of 3-chloro-N-(3-chloro-4-methoxyphenyl)-2-nitroaniline 1.00 g (26 mmol) of sodium hydride (purity 62.3%) was suspended in THF 10 ml, and 3-chloro-4-methoxyaniline 3.78 g (24 mmol) was added at 70° C. under a nitrogen gas stream, followed by stirring at the same temperature for 2 hours. After cooling to room temperature, the reaction solution obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure. When checked by gas chromatography, the peak of targeted compound was confirmed. The resulting crude product was purified by column chromatography to give the targeted 3-chloro-N-(3-chloro-4-methoxyphenyl)-2-nitroaniline 2.51 g as red crystal (yield 77%).

$^1$H-NMR (300 MHz, CDCl$_3$) δ: 6.89-7.47 (m, 7H), 3.92 (s, 3H) ppm

Example 19

Production of 3-chloro-N$^1$-(4-methoxyphenyl)benzene-1,2-diamine

3-Chloro-N-(4-methoxyphenyl)-2-nitroaniline 235.6 g (0.85 mol) was dissolved in toluene 800 ml and water 350 ml, and iron powder 236.4 g (4.4 mol) and acetic acid 35 ml were added thereto, followed by stirring vigorously with mechanical stirrer at 130° C. for 4 hours. After completing the reaction, the reaction solution was filtered using a filter aid, and the filtrate was extracted with toluene. The organic phase was washed 3 times with 10% aqueous sodium hydroxide solution 1 L. After drying over anhydrous sodium sulfate, the solvent was distilled away under reduced pressure to give 3-chloro-N$^1$-(4-methoxyphenyl)benzene-1,2-diamine 205.6 g as brown crystal (yield 98%).

Melting point: 65-66° C.

$^1$H-NMR (300 MHz, CDCl$_3$) δ: 7.02 (dd, J=8.0 Hz, J=1.1 Hz, 1H), 6.90 (dd, J=8.0 Hz, J=1.1 Hz, 1H), 6.83 (d, J=9.0 Hz, 2H), 6.78 (d, J=9.0 Hz, 2H), 6.64 (dd, J=8.0 Hz, J=8.0 Hz, 1H), 5.03 (s, 1H), 4.08 (s, 2H), 3.77 (s, 3H) ppm Example 20

Production of ethyl 5-chloro-1-(4-methoxyphenyl)-2-oxo-1,2-dihydroquinoxaline-3-carboxylate 3-Chloro-N$^1$-(4-methoxyphenyl)benzene-1,2-diamine 205.6 g (0.83 mol) was dissolved in toluene 1 L, and diethyl ketomalonate 173.2 g (1.0 mol) was added thereto, followed by refluxing for 2 hours with removing the water formed using Dean-Stark apparatus. After completing the reaction, the reaction solution was cooled to room temperature, and left overnight as it is to precipitate crystals of by-product. The by-product was separated by filtration, and after washing the reaction solution twice with 10% hydrochloric acid 1 L, dried over anhydrous sodium sulfate, then the solvent was distilled away under reduced pressure to give crude product. The crude product was recrystallized from ethyl alcohol to give ethyl 5-chloro-1-(4-methoxyphenyl)-2-oxo-1,2-dihydroquinoxaline-3-carboxylate 213.4 g as white crystal (yield 72%).

Melting point: 128-129° C.

$^1$H-NMR (300 MHz, CDCl$_3$) δ: 7.44 (dd, J=8.2 Hz, J=2.5 Hz, 1H), 7.34 (dd, J=8.2 Hz, J=8.2 Hz, 1H), 7.19 (d, J=9.6 Hz, 2H), 7.10 (d, J=9.6 Hz, 2H), 6.69 (dd, J=8.2 Hz, J=2.5 Hz, 1H), 4.51 (q, J=7.1 Hz, 2H), 3.89 (s, 3H), 1.43 (t, J=7.1 Hz, 3H) ppm Example 21

Production of 5-chloro-1-(4-methoxyphenyl)-2-oxo-1,2-dihydroquinoxaline-3-carboxylic acid Ethyl 5-chloro-1-(4-methoxyphenyl)-2-oxo-1,2-dihydroquinoxaline-3-carboxylate 213.4 g (0.6 mol) was dissolved in dioxane 350 ml and water 350 ml, and potassium carbonate 90.6 g (0.66 mol) was added thereto, followed by stirring at 110° C. for 3 hours. After completing the reaction, dioxane was distilled away under reduced pressure, and the aqueous layer was washed twice with ethyl acetate 1 L. Then, 6N hydrochloric acid was added to the aqueous layer to make pH<4, and the precipitated crystals were collected by filtration, and dried to give 5-chloro-1-(4-methoxyphenyl)-2-oxo-1,2-dihydroquinoxaline-3-carboxylic acid 192.0 g as white crystal (yield 97%).

Melting point: 198-200° C.

$^1$H-NMR (300 MHz, CDCl$_3$) δ: 13.62 (s, 1H), 7.62 (dd, J=8.5 Hz, J=1.4 Hz, 1H), 7.52 (dd, J=8.5 Hz, J=8.5 Hz, 1H), 7.22 (d, J=9.1 Hz, 2H), 7.17 (d, J=9.1 Hz, 2H), 6.82 (dd, J=8.5 Hz, J=1.4 Hz, 1H), 3.93 (s, 3H) ppm Example 22

Production of 5-chloro-1-(4-methoxyphenyl)-2-oxo-1,2-dihydroquinoxaline-3-carbonyl chloride 5-Chloro-1-(4-methoxyphenyl)-2-oxo-1,2-dihydroquinoxaline-3-carboxylic acid 192.0 g (0.58 mol) was dissolved in methylene chloride 800 ml, and oxalyl chloride 96 g (0.75 mol) and 2 drops of DMF (N,N-dimethylformamide) were added thereto, followed by stirring at 40° C. for 2 hours. After completing the reaction, the solvent was distilled away, then toluene (500 ml×2) was added, and excess oxalyl chloride was removed azeotropically to give 5-chloro-1-(4-methoxyphenyl)-2-oxo-1,2-dihydroquinoxaline-3-carbonyl chloride. The crude product obtained was used as it is to the next reaction.

Melting point: 131-134° C.

$^1$H-NMR (300 MHz, CDCl$_3$) δ: 7.50 (d, J=7.9 Hz, 1H), 7.43 (dd, J=7.9 Hz, J=7.9 Hz, 1H), 7.18 (d, J=9.0 Hz, 2H), 7.15 (d, J=9.0 Hz, 2H), 6.72 (d, J=8.3 Hz, 1H), 3.90 (s, 3H) ppm

Example 23

Production of 5-chloro-3-(2-hydroxy-6-oxo-1-cyclohexenecarbonyl)-1-(4-methoxyphenyl)quinoxaline-2-(1H)-one 5-Chloro-1-(4-methoxyphenyl)-2-oxo-1,2-dihydroquinoxaline-3-carbonyl chloride 202.5 g (0.58 mol) was dissolved in methylene chloride 800 ml, and cooled to 0° C. under a nitrogen gas stream. To the reaction solution, a solution of 1,3-cyclohexanedione 84.8 g (0.75 mol) and triethylamine 88.3 g (0.87 mol) dissolved in methylene chloride 250 ml was added dropwise at temperatures below 10° C. After finishing the dropping, the solution was stirred at room temperature for 3 hours. Then, triethylamine 88.3 g (0.87 mol) and acetone cyanohydrin 5.0 g (0.06 mol) were added to the reaction solution, and stirred overnight. After completing the reaction, the reaction solution was washed 3 times with 10% hydrochloric acid 1 L, dried over anhydrous sodium sulfate, then the solvent was distilled away under reduced pressure to give crude product. The crude product was washed with ethyl acetate to give 5-chloro-3-(2-hydroxy-6-oxo-1-cyclohexenecarbonyl)-1-(4-methoxyphenyl)quinoxaline-2-(1H)-one 227.9 g as white crystal (yield 93%).

Melting point: 249-251° C.

$^1$H-NMR (300 MHz, CDCl$_3$) δ: 16.23 (s, 1H), 7.39 (m, 1H), 7.25-7.30 (m, 3H), 7.09 (m, 2H), 6.71 (d, J=8.4 Hz, 1H), 3.88 (s, 3H), 2.75 (t, J=12.6 Hz, 2H), 2.44 (brs, 2H), 2.06 (t, J=12.9 Hz, 2H) ppm 5-Chloro-3-(2-hydroxy-6-oxo-1-cyclohexenecarbonyl)-1-(4-methoxyphenyl)quinoxaline-2-(1H)-one produced in Example 23 has an excellent herbicidal activity as described in WO2009/016841 listed in the Patent Document, and is industrially useful.

Comparison Example 1

Study on Production Method of 3-chloro-N-(4-methoxyphenyl)-2-nitroaniline

Method Described in Reference Example 7(1) of WO2009/016841 (Patent Document 1)

2,6-Dichloronitrobenzene 2.0 g (10 mmol) and p-anisidine 1.41 g (11 mmol) was dissolved in DMF (N,N-dimethylformamide) 15 ml, and potassium carbonate 1.73 g (13 mmol) was added thereto, followed by stirring with heating at 75° C. for 12 hours. The reaction mixture was poured into water, and extracted with ethyl acetate. The extracted organic phase was washed sequentially with water, 10% hydrochloric acid, water and saturated brine, and after drying over anhydrous magnesium sulfate, concentrated under reduced pressure, and then confirmed with gas chromatography and NMR, which was found to be a recovery of raw material.

$^1$H-NMR (300 MHz, CDCl$_3$) δ: 7.37-7.50 (m, 3H) ppm

Comparison Example 2

Study on Production of 3-chloro-N-(4-methoxyphenyl)-2-nitroaniline

Production Method of J. Med. Chem., vol. 32, p. 2573-2582 (1989)

p-Anisidine 1.28 g (10 mmol) was dissolved in THF 15 ml, and 0.60 g (16 mmol) of sodium hydride (purity 62.3%) was added thereto at room temperature. The solution was stirred for 10 minutes at room temperature. 2,6-Dichloronitrobenzene 2.0 g (10 mmol) was added thereto at room temperature. The reaction solution obtained was stirred for 12 hours at room temperature under nitrogen gas atmosphere. After stirring, the reaction solution was poured into water 150 ml and concentrated hydrochloric acid 10 ml, then extracted with ethyl acetate (100 ml×2). The organic phase obtained was washed with saturated brine, dried over anhydrous magnesium sulfate, concentrated under reduced pressure, then checked by gas chromatography, but the peak of targeted compound was not detected. When checked with NMR, only raw material, 2,6-dichloronitrobenzene, was confirmed, that is, it was confirmed that the desired reaction didn't proceed.

$^1$H-NMR (300 MHz, CDCl$_3$) δ: 7.37-7.50 (m, 3H) ppm

Comparison Example 3

Study on Production of 3-chloro-N-(4-methoxyphenyl)-2-nitroaniline 1.00 g (26 mmol) of sodium hydride (purity 62.3%) was suspended in DMF (N,N-dimethylformamide) 10 ml, and p-anisidine 2.95 g (24 mmol) was added at 70° C. under a nitrogen gas stream, followed by stirring at the same temperature for 2 hours. Then, after cooling to room temperature, the reaction solution obtained was added dropwise at 10~15° C. to a solution of 2,6-dichloronitrobenzene 2.0 g (10 mmol) in DMF 15 ml. After finishing the dropping, the solution was stirred at 10~15° C. for 1 hour, and the obtained reaction mixture was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure, then checked by gas chromatography, but the peak of targeted compound was not detected. When checked with NMR, only raw material, 2,6-dichloronitrobenzene, was confirmed, that is, it was confirmed that the desired reaction didn't proceed.

Comparison Example 4

Study on Production of 3-chloro-N-(4-methoxyphenyl)-2-nitroaniline 1.00 g (26 mmol) of sodium hydride (purity 62.3%) was suspended in NMP (N-methylpyrrolidone) 10 ml, and p-anisidine 2.95 g (24 mmol) was added at 70° C. under a nitrogen gas stream, followed by stirring at the same temperature for 2 hours. Then, after cooling to room temperature, the reaction mixture obtained was added dropwise at 10~15° C. to a solution of 2,6-dichloronitrobenzene 2.0 g (10 mmol) in NMP 15 ml. After finishing the dropping, the solution was stirred at 10~15° C. for 1 hour, and the obtained reaction mixture was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure, then checked by gas chromatography, but the peak of targeted compound was not detected. When checked with NMR, only raw material, 2,6-dichloronitrobenzene, was confirmed, that is, it was confirmed that the desired reaction didn't proceed.

$^1$H-NMR (300 MHz, CDCl$_3$) δ: 7.37-7.50 (m, 3H) ppm

Comparison Example 5

Study on Production of
3-chloro-N-(4-methoxyphenyl)-2-nitroaniline 1.00 g (26 mmol) of sodium hydride (purity 62.3%) was suspended in DMF (N,N-dimethylformamide) 10 ml, and p-anisidine 2.95 g (24 mmol) was added at 70° C. under a nitrogen gas stream, followed by stirring at the same temperature for 2 hours. The resulting reaction mixture was cooled to −20° C., and a solution of 2,6-dichloronitrobenzene 2.0 g (10 mmol) in DMF 15 ml was added dropwise thereto with keeping the inner temperature from exceeding −20° C. After finishing the dropping, the solution was stirred at −20~-25° C. for 30 minutes, then warmed to room temperature. The obtained reaction solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure, then checked by gas chromatography, but the peak of targeted compound was not detected. When checked with NMR, only raw material, 2,6-dichloronitrobenzene, was confirmed, that is, it was confirmed that the desired reaction didn't proceed.

$^1$H-NMR (300 MHz, CDCl$_3$) δ: 7.37-7.50 (m, 3H) ppm

Comparison Example 6

Study on Production of
3-chloro-N-(4-methoxyphenyl)-2-nitroaniline 1.00 g (26 mmol) of sodium hydride (purity 62.3%) was suspended in NMP (N-methylpyrrolidone) 10 ml, and p-anisidine 2.95 g (24 mmol) was added at 70° C. under a nitrogen gas stream, followed by stirring at the same temperature for 2 hours. The resulting reaction mixture was cooled to −20° C., and a solution of 2,6-dichloronitrobenzene 2.0 g (10 mmol) in NMP 15 ml was added dropwise thereto with keeping the inner temperature from exceeding −20° C. After finishing the dropping, the solution was stirred at −20~-25° C. for 30 minutes, then warmed to room temperature. The obtained reaction solution was poured into water 150 ml and concentrated hydrochloric acid 10 ml, then extracted with ethyl acetate (100 ml×2). The organic phase obtained was washed with saturated brine, dried over anhydrous magnesium sulfate, and concentrated under reduced pressure, then checked by gas chromatography, but the peak of targeted compound was not detected. When checked with NMR, only raw material, 2,6-dichloronitrobenzene, was confirmed, that is, it was confirmed that the desired reaction didn't proceed.

$^1$H-NMR (300 MHz, CDCl$_3$) δ: 7.37-7.50 (m, 3H) ppm

Comparison Example 7

Study on Production of 3-(3-chloro-2-nitrophenylamino)-4-cyano-1-methylpyrazole 1.00 g (26 mmol) of sodium hydride (purity 62.3%) was suspended in THF 10 ml, and 3-amino-1-methylpyrazole-4-carbonitrile 2.88 g (24 mmol) was added at 70° C. under a nitrogen gas stream, followed by stirring at the same temperature for 2 hours. Then, after cooling to room temperature, the reaction mixture obtained was added dropwise at 10~15° C. to a solution of 2,6-dichloronitrobenzene 2.0 g (10 mmol) in THF 15 ml. After finishing the dropping, the solution was stirred at 10~15° C. for 1 hour, and the obtained reaction mixture was poured into water 150 ml and concentrated hydrochloric acid 10 ml, then extracted with ethyl acetate (100 ml×2). The ethyl acetate phase obtained was washed with saturated brine, dried over anhydrous magnesium sulfate, and concentrated under reduced pressure. When checked by gas chromatography, the peak of targeted compound was not detected. When checked with NMR, only raw material, 2,6-dichloronitrobenzene, was confirmed, thus the desired reaction didn't proceed.

$^1$H-NMR (300 MHz, CDCl$_3$) δ: 7.37-7.50 (m, 3H) ppm

Comparison Example 8

Study on Production of 3-(3-chloro-2-nitrophenylamino)-4-cyano-1-methylpyrazole

Production method of J. Med. Chem., vol. 32, p. 2573-2582 (1989)

3-Amino-1-methylpyrazole-4-carbonitrile 1.27 g (10 mmol) was dissolved in THF 15 ml, and 0.60 g (16 mmol) of sodium hydride (purity 62.3%) was added thereto at room temperature. The solution was stirred for 10 minutes at room temperature. 2,6-Dichloronitrobenzene 2.0 g (10 mmol) was added thereto at room temperature. The reaction solution obtained was stirred for 12 hours at room temperature under nitrogen gas atmosphere. After stirring, the reaction solution was poured into water 150 ml and concentrated hydrochloric acid 10 ml, then extracted with ethyl acetate (100 ml×2). The ethyl acetate phase obtained was washed with saturated brine, dried over anhydrous magnesium sulfate, and concentrated under reduced pressure. When checked by gas chromatography, the peak of targeted compound was not detected. When checked with NMR, the obtained was a mixture of 2,6-dichloronitrobenzene and 3-amino-1-methylpyrazole-4-carbonitrile.

$^1$H-NMR (300 MHz, CDCl$_3$) δ: 2,6-dichloronitrobenzene; 7.37-7.50 (m, 3H) ppm 3-amino-1-methylpyrazole-4-carbonitrile; 4.09 (brs, 3H), 3.73 (s, 3H) ppm

Comparison Example 9

Study on Production of
3-chloro-N-(4-methoxyphenyl)-2-nitroaniline

Production from N-(4-methoxyphenyl)formamide 1.00 g (26 mmol) of sodium hydride (purity 62.3%) was suspended in NMP (N-methylpyrrolidone) 5 mL, and N-(4-methoxyphenyl)formamide 3.62 g (24 mmol) was added at room temperature under a nitrogen gas stream. After stirring for 1 hour at room temperature, 2,6-dichloronitrobenzene 2.0 g (10 mmol) was added at room temperature, and the reaction solution obtained was stirred for 20 hours at room temperature. The reaction solution was heated to 140° C., and stirred with heating for 10 hours. When checked by gas chromatography, the peak of targeted compound was detected, thus the reaction solution was cooled to room temperature, and poured into water 150 mL and concentrated hydrochloric acid 10 mL, then extracted with ethyl acetate (100 mL×2). The ethyl acetate phase obtained was washed with saturated brine, dried over anhydrous magnesium sulfate, and concentrated under reduced pressure. Then MeOH 20 mL and concentrated hydrochloric acid 3 mL were added, and refluxed with heating for 30 minutes. After completing the reaction, the solvent was concentrated, and poured again into water 150 mL and concentrated hydrochloric acid 10 mL, then extracted with ethyl acetate (100 mL×2). The ethyl acetate phase obtained was washed with saturated brine, dried over anhydrous magnesium sulfate, and concentrated under reduced pressure. The crude product was purified by column chromatography to give the targeted compound 1.08 g (yield 39%).

(Gas Chromatographic Assay Method)

About the detail of gas chromatographic assay method mentioned above, the following documents can be referred to, if necessary.

(a) The Chemical Society of Japan, ed., Shinjikken Kagaku Koza 9, Bunseki Kagaku II, pp. 60-86 (1977), published by Iiizumi Shingo, Maruzen Co., Ltd.

(b) The Chemical Society of Japan, ed., Jikken Kagaku Koza 20-1, Bunseki Kagaku, $5^{th}$ ed., pp. 121-129 (2007), published by Murata Seishiro, Maruzen Co., Ltd. (For example, about the specific usage and condition of gas chromatographic assay, page 123 to 127 can be referred to.)

(HPLC Assay Method)

About the detail of HPLC assay method mentioned above, the following documents can be referred to, if necessary.

(a) The Chemical Society of Japan, ed., Shinjikken Kagaku Koza 9, Bunseki Kagaku II, pp. 86-112 (1977), published by Iiizumi Shingo, Maruzen Co., Ltd. (For example, about the combination of packing material and mobile phase usable for column, page 93 to 96 can be referred to.)

(b) The Chemical Society of Japan, ed., Jikken Kagaku Koza 20-1, Bunseki Kagaku, $5^{th}$ ed., pp. 130-151 (2007), published by Murata Seishiro, Maruzen Co., Ltd. (For example, about the specific usage and condition of reversed phase chromatographic assay, page 135 to 137 can be referred to.)

INDUSTRIAL APPLICABILITY

According to the present invention, a novel industrial method for producing diphenylamine compounds can be provided.

In the method of the present invention, it is possible to use the above-mentioned 2,6-dichloronitrobenzene compound represented by general formula (1) as raw material, therefore diphenylamine compounds can be produced with a convenient operation under a mild condition by using an industrially easily-available reagent, without using expensive catalysts and reagents, inexpensively, and further without using specialized reaction apparatus.

In addition, in the method of the present invention, the formation of by-products is suppressed, and a highly-pure diphenylamine compound can be produced with a high yield and efficiently on an industrial scale. The suppression of by-products results in a reduction of environmental burdens.

Furthermore, since the method of the present invention does not generate harmful wastes derived from transition metal such as noble metal catalysts, disposal of wastes is easy, and it is friendly to the environment.

The diphenylamine compounds represented by general formula (3) obtained by the method of the present invention are useful as medicine and agricultural chemicals and intermediates thereof, functional pigments, electronic materials and the like and intermediates thereof. For example, 5-chloro-3-(2-hydroxy-6-oxo-1-cyclohexenecarbonyl)-1-(4-methoxyphenyl)quinoxaline-2-(1H)-one produced in Example 23 has an excellent herbicidal activity as described in WO2009/016841 listed in the Patent Document, and is industrially useful. Thus, the method of the present invention has an industrially high utility value.

The invention claimed is:

1. A method for producing diphenylamine compounds represented by general formula (3):

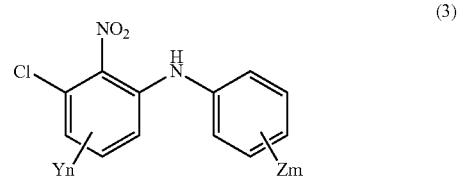

(3)

wherein, Z represents methoxy group at the para position of amine; m is 1; which is characterized by reacting aniline compounds represented by general formula (2):

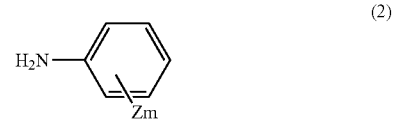

(2)

wherein, Z and m are as defined above; under the presence of base and ethers solvent, with 2,6-dichloronitrobenzene compound represented by general formula (1):

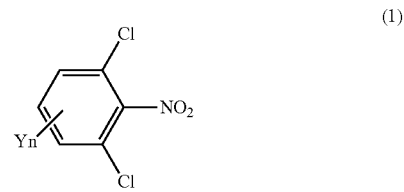

(1)

wherein Y is halogen and n represents an integer of 0, wherein 2.0 moles or more of aniline compound represented by general formula (2) is used relative to 1 mole of 2,6-dichloronitrobenzene compound represented by general formula (1) and 2.0 equivalents or more of base is used relative to 1 mole of 2,6-dichloronitrobenzene compound represented by general formula (1).

2. The method for producing diphenylamine compounds according to claim 1, wherein the ethers solvent is tetrahydrofuran.

3. The method for producing diphenylamine compounds according to claim 1, wherein the base is alkali metal hydride or alkali metal.

4. The method for producing diphenylamine compounds according to claim 1, wherein the base is sodium hydride or sodium metal.

5. The method for producing diphenylamine compounds according to claim 1, wherein the base is sodium hydride.

* * * * *